United States Patent [19]
Simmons et al.

[11] Patent Number: 5,795,989
[45] Date of Patent: Aug. 18, 1998

[54] FABRIC ABRASION TESTER AND ASSOCIATED ABRADING METHODS

[75] Inventors: Harry Evans Simmons; Khalid Ahmad Achagzai, both of Charlotte, N.C.

[73] Assignee: Industrial Laboratory Equipment Co., Inc., Charlotte, N.C.

[21] Appl. No.: 833,285

[22] Filed: Apr. 4, 1997

[51] Int. Cl.⁶ .................................................. G01N 3/56
[52] U.S. Cl. ................................................................ 73/7
[58] Field of Search .................................. 73/7, 9, 159

[56] References Cited

U.S. PATENT DOCUMENTS

| | | |
|---|---|---|
| 2,251,681 | 8/1941 | Hathaway et al. |
| 2,311,430 | 2/1943 | Beno. |
| 2,815,658 | 12/1957 | Press. |
| 2,895,326 | 7/1959 | Fesperman et al. |
| 3,208,265 | 9/1965 | Rutledge ............................ 73/7 |
| 3,721,115 | 3/1973 | Kearns ............................... 73/9 |
| 3,835,697 | 9/1974 | Schneider et al. |
| 4,462,245 | 7/1984 | Gould et al. |
| 4,936,135 | 6/1990 | Annis et al. |
| 5,557,039 | 9/1996 | Annis et al. |

FOREIGN PATENT DOCUMENTS

| | | |
|---|---|---|
| 873 315 | 4/1953 | Germany. |
| 1146265 | 7/1967 | United Kingdom. |

OTHER PUBLICATIONS

Standard Test Method for Pilling Resistance and Other Related Surface Changes of Textiles Fabrics (Martindale Pressure Tester Method), American Society for Testing and Materials (ASTM) Designation D4970–89; *Annual Book of ASTM Standards*.

Standard Test Method for Abrasion Resistance of Textile Fabrics (Oscillatory Cylinder Method), American Society for Testing and Materials (ASTM) Designation D4157–92; *Annual Book of ASTM Standards*.

Standard Test Method for Abrasion Resistance of Textile Fabrics (Flexing and Abrasion Method), American Society for Testing and Materials (ASTM) Designation D 3885–92; *Annual Book for ASTM Standards*.

Standard Test Method for Abrasion Resistance of Textile Fabrics (Uniform Abrasion Method), American Society for Testing and Materials (ASTM) Designation D4158–92; *Annual Book of ASTM Standards*.

Standard Test Method for Abrasion Resistance of Textile Fabrics (Martindale Abrasion Tester Method), American Society for Testing and Materials (ASTM) Designation D4966–89; *Annual Book of ASTM Standards*.

Standard Test Method for Abrasion Resistance of Textile Fabrics (Rotary Platform, Double-Head Method), American Society for Testing and Materials (ASTM) Designation D3884–92; *Annual Book of ASTM Standards*.

*Primary Examiner*—Robert Raevis
*Attorney, Agent, or Firm*—Bell Seltzer Intellectual Property Law Group Alston & Bird LLP

[57] ABSTRACT

The fabric abrasion testing device abrades a fabric sample in a predetermined manner such that the abrading process can be accurately and efficiently observed without halting the abrasion testing. The abrasion testing device includes at least one fabric sample holder for supporting the fabric sample. The abrasion testing device also includes an optically transmissive motion plate that, in a preferred embodiment, securely mounts an abrasion element having a removably engaged abrasive surface for abrading the fabric sample. The operator can therefore look through the motion plate to observe fabric wear during ongoing abrasion tests. The optically transmissive motion plate is operably connected to a motor for moving the motion plate and, in turn, the element mounted therethrough in a predetermined pattern relative to the fabric sample. The fabric sample holder can be a pedestal having at least a partially optically transmissive upper surface and a light source for backlighting the fabric sample, thereby further facilitating observation of an ongoing abrasion process.

15 Claims, 4 Drawing Sheets

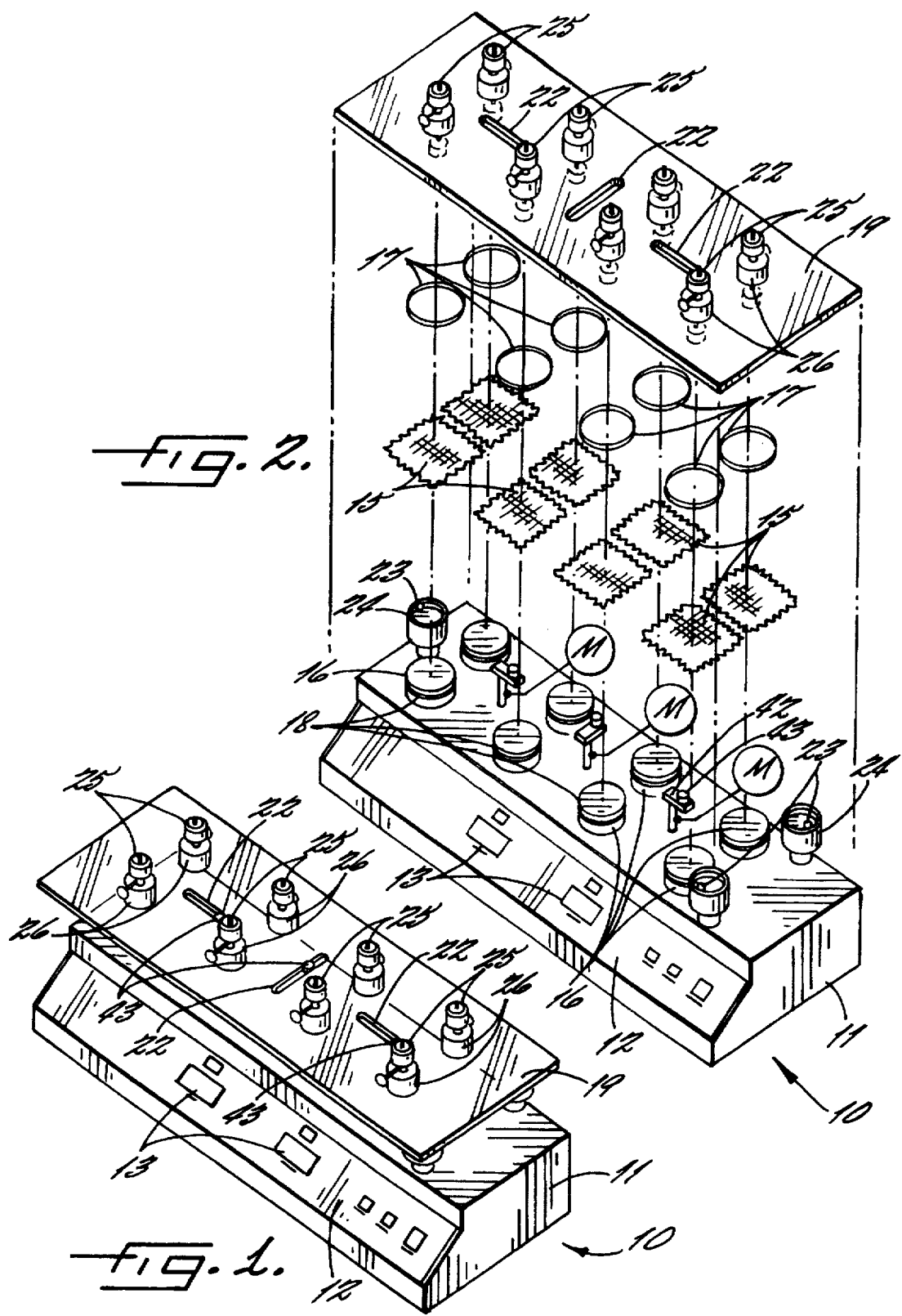

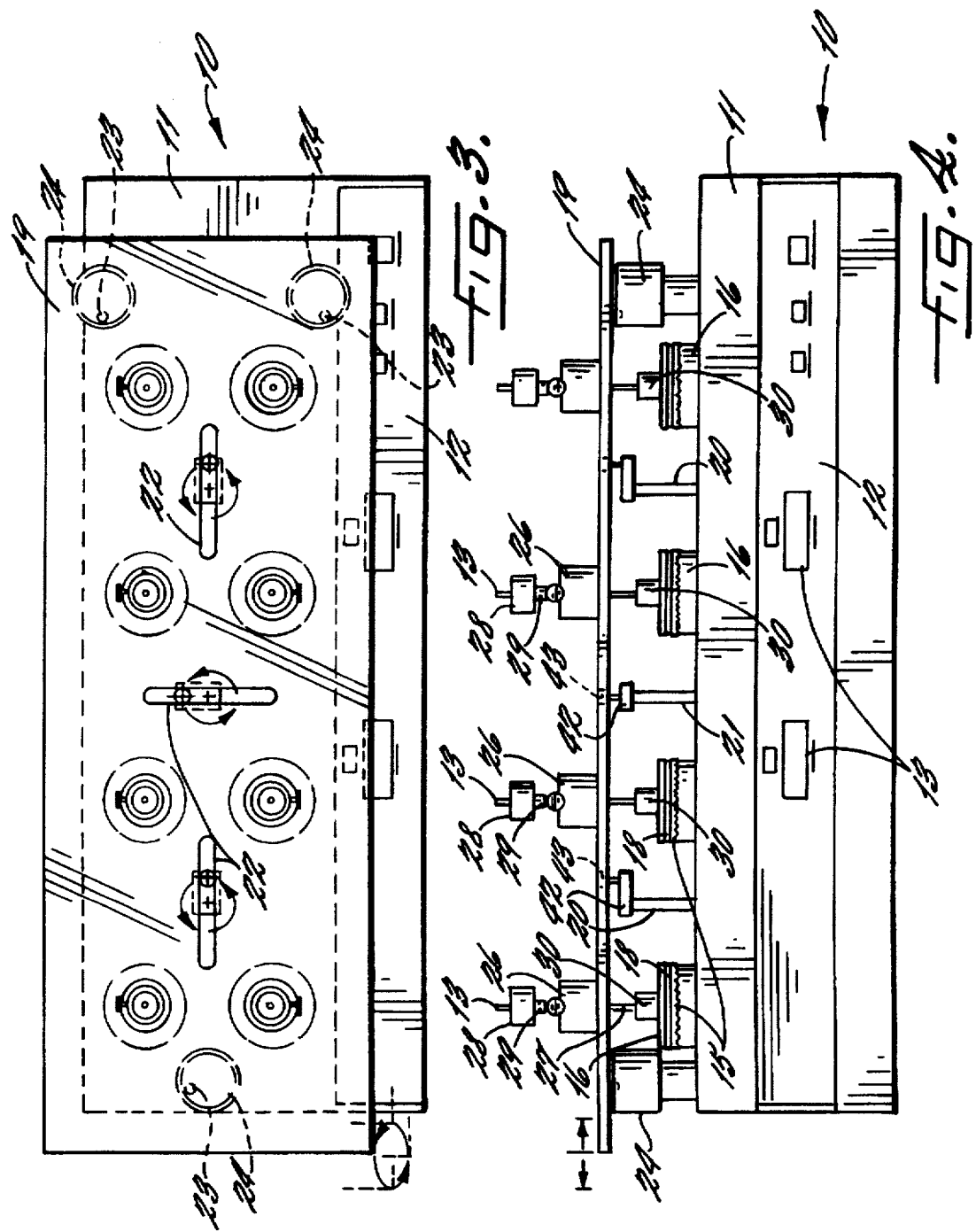

5,795,989

1

FABRIC ABRASION TESTER AND ASSOCIATED ABRADING METHODS

FIELD OF THE INVENTION

The present invention relates to the abrasion testing of fabrics and more particularly, relates to an improved abrasion tester and associated abrading methods.

BACKGROUND OF THE INVENTION

Conventional fabric abrasion testers and specifically, Martindale-type abrasion testers are used to measure the wear and, hence, the durability of both woven and knitted fabrics. Fabric abrasion, or specifically abrasion resistance, is typically measured in terms of the number of cycles on a specified machine and is an indication of the number of strokes or passes of an abradant against the test fabric prior to wearing a hole in the fabric or reaching some other predefined level of wear.

Martindale-type abrasion testers consist of a base including one or more sample holders for holding the test fabric in place during abrasion testing. The test fabric is generally set at a predetermined tension and maintained at that tension by securing the test fabric onto the sample holder with a circular bracket. Martindale-type abrasion testers also include one or more weighted pistons which overlie and correspond to respective sample holders. The weighted pistons are typically fitted with either a permanent or disposable abradant and are lowered into contact with the fabrics mounted upon the corresponding sample holders. The weighted pistons are then moved in a rotating elliptical or Lissajous-type pattern along the test fabric with each full revolution constituting one stroke. The weights provide a constant pressure between the abrasive fabric and the test fabric. The pistons are mounted within a motion plate, typically made of metal, which is translated in two different directions by the gear assemblies of the Martindale-type testing device. A Martindale-type abrasion tester also includes ball bearings that are provided in bearing cups to support the motion plate and to facilitate the movement of the motion plate relative to the base.

The testing process on a Martindale-type abrasion tester continues until there is a visible change in the fabric, such as two or more broken threads in a woven fabric, a hole appearing in a knitted fabric, or a discernible change in shade or appearance that would be sufficient to cause a customer to complain. In order to determine wear on the test fabric, the motion plate must be removed. Removing the motion plate, however, is labor intensive and time consuming, but more importantly, it can be disruptive to the testing process as the test fabric must be checked periodically until the testing is completed.

During abrasion testing, permanent abradants, such as hardened metal, may pick up finishing or other material from the test fabric and must be cleaned at frequent intervals. Disposable abradants, on the other hand, are typically used only once or are discarded after limited use. In either case, the abradant must periodically be checked and, if necessary, cleaned or replaced. In order to remove the abradant for maintenance, the motion plate must be lifted and the pistons holding the abradant must be taken apart, both of which can be labor intensive and time consuming. Furthermore, lifting the motion plate can cause the piston weights to fall when the plate is angled during lifting.

In seeking better apparatus for testing the wearability of fabrics, several other types of fabric abrasion testers have been developed. One such example of a fabric abrasion tester is disclosed in U.S. Pat. No. 5,557,039 to Annis, et al., which discloses an abrasion tester having a fabric sample base capable of rotation in 5° increments to change the direction of abrasion. The abrasion tester has a clear Plexiglas® cover that protects the operator from moving parts. In order to further protect the operator, the cover is operably connected to a safety switch to prevent operation of the apparatus while the cover is open. While the cover provides protection, the cover is not an active component of the abrader since the cover remains stationary during the abrasion process and does not contribute to the abrasion of the fabric sample.

A variety of other testers are also known in the art. Examples include a rotary platform double head abrader that abrades a fabric specimen using abrasive wheels attached to a pair of pivoted arms in conjunction with a flat-circular specimen holder rotated by a motor. A flexing and abrasive tester abrades a fabric sample by folding the sample around a flexing bar or a folding blade and then securing the ends of the sample to an upper stationary plate and a lower reciprocating plate, respectively. An oscillating cylinder abrasive machine abrades fabric specimens using a sheet of abrasive material mounted on an oscillating cylinder. A uniform abrader abrades a fabric specimen by rotating the specimen at very nearly, but not quite, the same angular velocity as the abradant, but non-coaxial axes such that each part of the specimen comes into contact with a different part of the abradant at each rotation.

Regardless of the type of abrasion tester, fabric samples must be viewed repeatedly during the abrasion process to determine the wear of the fabric sample. However, conventional abrasion testers, such as Martindale-type abrasion testers, typically require the abrasion process to be halted and the motion plate to be lifted in order to view the fabric sample. As a result, conventional abrasion testing processes can be unnecessarily labor intensive and time consuming.

SUMMARY OF THE INVENTION

The present invention provides a fabric abrasion testing device for abrading a fabric sample in a predetermined manner whereby the ongoing abradant process can be easily observed without halting the abrasion testing and dismantling the abrasion tester. The abrasion testing device includes at least one fabric sample holder for supporting the fabric sample. The abrasion testing device also includes at least one abrasion element corresponding to the fabric sample holder and having an abrasive surface for abrading the fabric sample.

Advantageously, the fabric abrasion testing device includes an optically transmissive motion plate typically formed of a translucent material or a transparent material, such that the abrasion of the fabric sample can be observed through the optically transmissive motion plate. The optically transmissive motion plate defines one or more apertures for mounting either the abrasion elements or the fabric sample holders therethrough. Thus, the optically transmissive motion plate permits an operator to view an ongoing abrasion test without having to halt the abrasion test and raise the motion plate, as required by conventional Martindale-type abrasion testers.

A motor, operably connected to the optically transmissive motion plate, is provided for moving the optically transmissive motion plate in a predetermined pattern. As a result, the elements mounted through the optically transmissive motion plate also move in a predetermined pattern relative to their corresponding elements, i.e., the elements not mounted through the optically transmissive motion plate. Consequently, the abrasion surfaces of the abrasion elements abrade the fabric samples mounted on the fabric sample holders. Preferably, the mounted element is weighted such as by a predetermined weight to facilitate the abrasion of the fabric sample.

In a preferred embodiment, the abrasion elements are mounted in the one or more apertures of the optically transmissive motion plate and thus through the optically transmissive motion plate. In this embodiment, the abrasion elements have an abrasive lower surface and a predetermined weight for urging the abrasive lower elements toward the fabric samples supported by the corresponding fabric sample holders. The motor thus moves the optically transmissive motion plate in a predetermined pattern relative to the fabric sample holders such that the abrasion elements also move in a predetermined pattern relative to the fabric samples mounted on corresponding fabric sample holders.

The fabric sample holder can be a pedestal having an upper surface for supporting the fabric sample. According to one embodiment, at least the upper portion of the pedestal is made of a material which is at least partially optically transmissive, such as a translucent material or a transparent material. Additionally, the fabric sample holder of this embodiment can include means for illuminating at least the upper portion of the pedestal such that the fabric sample supported by the fabric sample holder is backlit, thereby permitting the operator to more readily view the abrasion of the fabric sample.

The abrasive lower surface of the abrasion element preferably includes an abradant having top and bottom surfaces. The bottom surface of the abradant has an abrasive texture for contacting the fabric sample, while the top surface typically includes an adhesive layer for removably engaging the lower surface of the abrasion element. The fabric abrasion testing device can also include means for securing the abrasion element in a raised position such that a used abradant can be replaced with a fresh abradant, by merely peeling the used abradant from the lower surface of the abrasion element and thereafter adhesively attaching the replacement abradant to the lower surface of the abrasion element.

Accordingly, there has been provided a fabric abrasion tester allowing for the efficient testing of the wearability of a fabric specimen in terms of time and labor with a minimization of disruptions to the testing process. In particular, as a result of the optically transmissive motion plate and/or the backlighting of the fabric sample, the fabric abrasion testing device and associated methods of the present invention permit the abrasion process to be monitored without halting the abrasion test and lifting the motion plate as required by conventional Martindale-type abrasion testers.

BRIEF DESCRIPTION OF THE DRAWINGS

The foregoing and other advantages and features of the invention, and the manner in which the same are accomplished, will become more readily apparent upon consideration of the following detailed description of the invention taken in conjunction with the accompanying drawings, which illustrate preferred and exemplary embodiments, and wherein:

FIG. 1 is a perspective view of a fabric abrasion tester of one embodiment of the present invention;

FIG. 2 is an exploded view further illustrating the embodiment of the fabric abrasion tester of FIG. 1;

FIG. 3 is top view of the fabric abrasion tester of FIG. 1 with directional arrows showing the elliptical movement of the motion plate;

FIG. 4 is a side view of the fabric abrasion tester of FIG. 1 with directional arrows showing the horizontal movement of the motion plate;

DETAILED DESCRIPTION OF THE PREFERRED EMBODIMENTS

Figure 5:
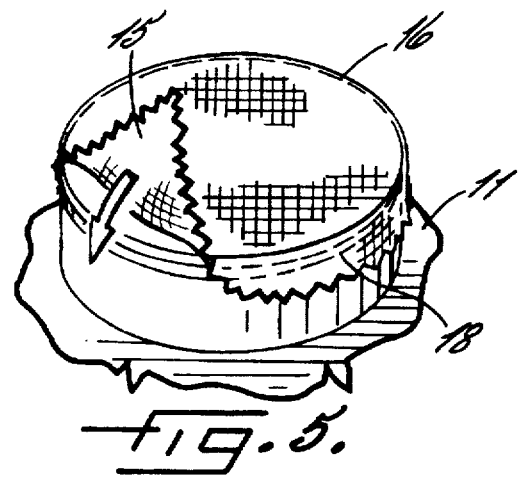
FIG. 5 is a perspective view of a fabric sample holder with a directional arrow showing the positioning of a fabric sample on the fabric sample holder.

The present invention will now be described more fully hereinafter with reference to the accompanying drawings, in which a preferred embodiment of the invention is shown. This invention may, however, be embodied in many different forms and should not be construed as limited to the embodiments set forth herein; rather, this embodiment is provided so that this disclosure will be thorough and complete and will fully convey the scope of the invention to those skilled in the art. Like numbers refer to like elements throughout.

Referring now to the drawings and in particular to FIG. 1, there is shown a fabric abrasion tester 10 and more specifically, an improved Martindale-type abrasion tester. The abrasion tester 10 includes an external housing 11 encasing a motor and a motor gearbox (not shown). As with a conventional Martindale-type abrasion tester, the housing 11 further includes a control panel 12 containing counters and various control switches. The counters measure the number of abrasion cycles and may include a batch set counter, a batch total counter and a grand total counter. The control switches may include power on/off, reset, stop/start, a timer and a keypad for setting the number of abrasion cycles desired on the batch set counter.

Figure 6:
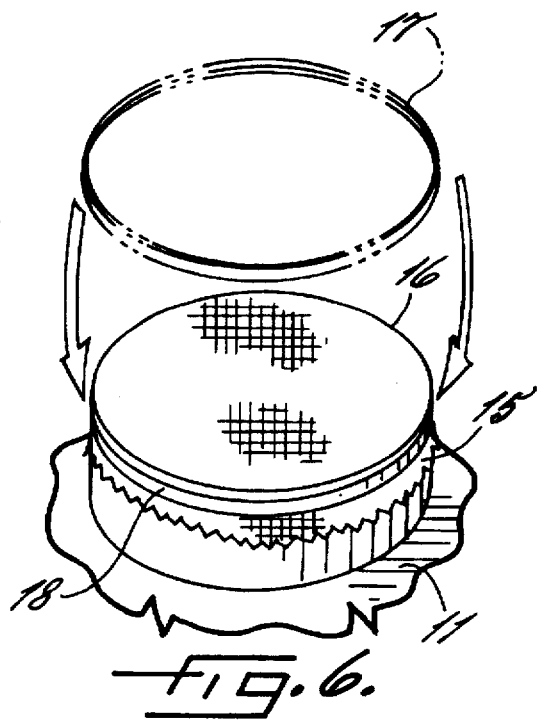
FIG. 6 is a partially exploded perspective view of a fabric sample holder with directional arrows showing the positioning of an elastomeric ring around the fabric sample to secure the fabric sample to the fabric sample holder.

As shown in FIG. 2, fabric sample holders 16 are secured to the top surface of the external housing 11. Although a fabric abrasion tester having eight fabric sample holders is illustrated, the fabric abrasion tester can include any number of fabric sample holders. In one preferred embodiment, the fabric sample holders 16 are cylindrical in shape, however, the fabric sample holders can have other shapes if desired. The individual test fabric samples 15 are secured to the fabric sample holders 16 in order to maintain a relatively constant tension across the surface of the fabric sample. As shown in FIGS. 5 and 6, the fabric samples 15 may be secured to the fabric sample holders 16 with elastomeric rings 17, such as rubber bands, which fit over the fabric samples and matingly engage grooves 18 defined by the sidewalls of the fabric sample holders. Alternately, the fabric samples 15 may be secured to the fabric sample holders 16 through other conventional means such as fasteners on the top surface and/or sidewalls of the fabric sample holders or by means of a circular bracket that fits over the fabric sample in a like manner to the elastomeric rings. Advantageously, the top surface of the fabric sample holder 16 may include a rough mounting surface, such as sandpaper, or a resiliently compressive structural material, such as polyurethane foam or cork which grips the fabric sample 15 and prevents the fabric sample from stretching or slipping during the abrasion process.

The abrasion tester 10 also includes a motion plate 19 that is operably connected to the motor and motor gearbox through two outer pegs 20 and an inner peg 21 which extend through the top surface of the housing 11 and are received within corresponding slots 22 of the motion plate. Although not illustrated, it will be appreciated that a lower end of each peg is operably connected to the motor within the housing so as to be rotated thereby. In addition, the upper end of each peg also generally includes an arm 42 that extends laterally from the peg and that includes a knob 43 for engaging the respective slot 22 defined by the motion plate 19.

The motion plate 19 is movably supported by ball bearings 23 contained within and supported by bearing cups 24. Thus, the motion plate can move relative to the housing. As is shown in FIGS. 3 and 4, the motor, through the motor gearbox, rotates the outer pegs 20 and the inner peg 21. As a result of the rotation of the outer pegs 20 and the inner peg 21, the motion plate 19 is moved in a Lissajous figure or elliptical pattern with each full revolution constituting one stroke. The Lissajous figure or elliptical pattern of the motion plate 19 is well known in the art as it pertains to Martindale-type abrasion testers.

The motion plate 19 is preferably formed of an optically transmissive material. For example, the motion plate is preferably formed of a material selected from a group consisting of a translucent material and a transparent material. Thus, the operator can observe the abrasion of the fabric sample 15 through the motion plate without having to halt the abrasion process and lift the motion plate as required by conventional Martindale-type abrasion testers. In one preferred embodiment, the motion plate 19 may be formed from either polycarbonate resins such as a LEXAN® material or a polymethyl methacrylate such as a PLEXIGLASS® material.

As shown in FIG. 4, the abrasion tester 10 also preferably includes mounting elements 26 on the top surface of the motion plate 19. The mounting elements may be secured to the top surface of the motion plate by conventional means or, alternatively, the mounting elements 26 may be constructed integrally with the motion plate 19. In either embodiment, the mounting elements are preferably also formed of an optically transmissive material.

Figure 7:
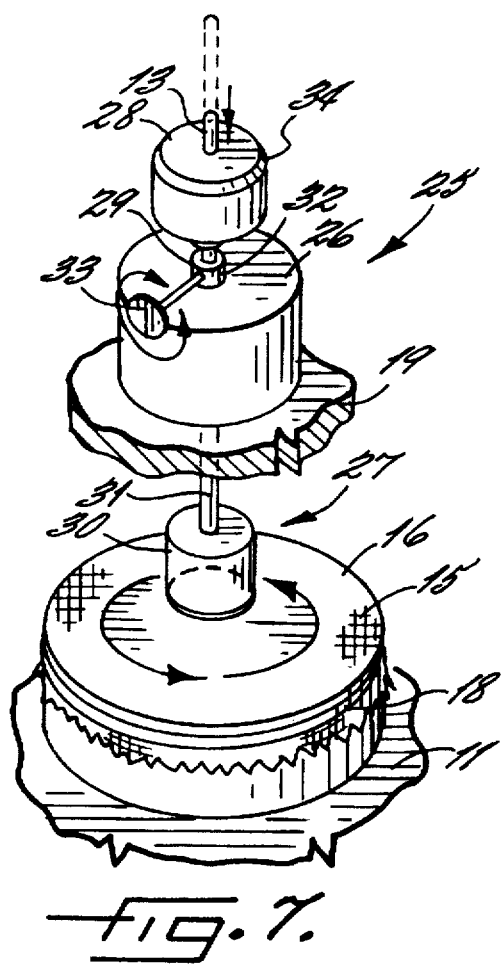
FIG. 7 is a fragmentary perspective view showing an abrasion element and a corresponding fabric sample holder with directional arrows showing movement of the shoe member and set screw.
Figure 8:
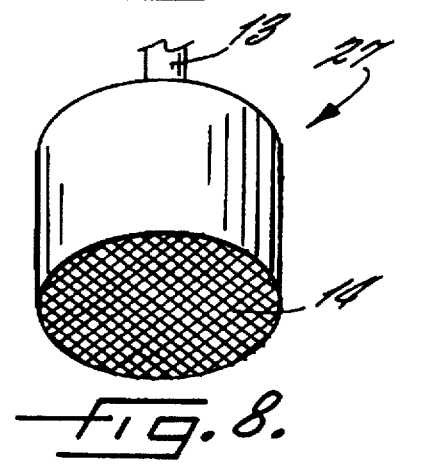
FIG. 8 is a fragmentary perspective view a shaft, shoe member and abradant.
Figure 9:
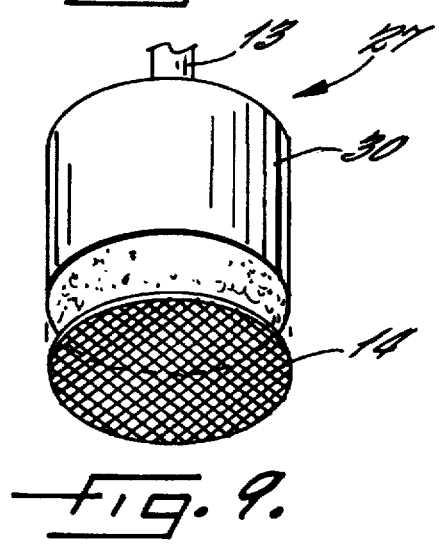
FIG. 9 is a fragmentary perspective view of a shaft and shoe member in which the abradant has been removed from the lower surface of the shoe member.

The abrasion tester 10 also includes an abrasion element 25 having a lower portion 27 and upper portion 28 connected by a shaft 13. Typically, the abrasion tester has the same number of abrasion elements as fabric sample holders since each abrasion element is aligned with and corresponds to a respective fabric sample holder. Each abrasion element is mounted in a respective aperture defined by a corresponding mounting element 26 and the motion plate 19 such that the lower portion of the abrasion element is below the motion plate, while the upper portion of the abrasion element is above the motion plate. As shown in FIGS. 7 and 8, the lower portion 27 of the abrasion element 25 includes a shoe member 30 connected to the shaft 13. The shoe member 30 has an abradant 14 secured to the underside of the shoe member. The abradant 14 may be integral with the shoe member 30 as shown in FIG. 8, thus forming a permanent abradant as is well known in the art. Alternately, as is shown in FIG. 9, an abradant 31 may be removably attached to the shoe member 30 through an adhesive backing applied either to the abradant or to the underside of the shoe member.

As is shown in FIG. 7, the corresponding upper portion 28 of each abrasion element 25 includes a weight 34. While other types of weights may be utilized, one typical weight has a centrally located aperture for slidably receiving the shaft 13. The weight 34 of the embodiment is supported laterally by the shaft 13 and vertically by a support element 29. The support element 29 may be secured to the shaft 13 by conventional threading or may be formed integrally. Accordingly, the shaft 13 should be of a sufficient length to extend from the shoe member 30 when lowered to the abrading position to a sufficient distance above the motion plate 19 so that the corresponding weight 34 can be reliably mounted upon the upper portion of the shaft.

As is shown in FIG. 7, the abrasion element of one advantageous embodiment further includes a tubular collar 32 and set screw 33 between the support element 29 and mounting element 26 to allow the user to temporarily elevate the shoe member 30 and replace the fabric sample 15 and/or the abradant. As shown, the collar is slidably fitted about the shaft, while the set screw extends through the collar and engagably contacts the shaft for securing the collar in a fixed position relative to the shaft.

When conducting an abrasion test, the operator positions the abradant 14 in frictional contact with the fabric sample 15 supported on the fabric sample holder 16 such that the underside of the shoe member 30 is in close proximity to and parallel with the top surface of the fabric sample holder as the motion plate and, in turn, the abradant, is moved relative to the fabric sample. In order to replace the fabric sample and/or the abradant, however, the abrading process is halted and the shoe member 30 is raised. Once the abrasion element 25 is in the raised position, the set screw 33 may be tightened to affix the collar to the shaft and to secure the abrasion element in a raised position. The operator can then replace or otherwise adjust the fabric sample 15. Additionally, as a removable abradant 31 deteriorates through use or a permanent abradant picks up material, the shoe member 30 may be temporarily raised to allow the operator amble space to service a permanent abradant or to detach an adhesively attached removable abradant and to adhesively attach a new or replacement abradant 31 to the lower surface of the shoe member. In this regard, the top surface of the removable abradant of the present invention preferably includes an adhesive layer for attaching the abradant to the lower surface of the shoe member as shown in FIG. 8. As such, the abradant 14 may be serviced without the necessity of removing the motion plate or deconstructing the abradant pistons of conventional Martindale-type abrasion testers.

During the abrasion testing process, the elliptical motion of the motion plate 19, results in the abrasion elements 25 mounted to the motion plate and the corresponding abradants 14 moving in a same predetermined pattern relative to the fabric samples 15 supported on the corresponding fabric sample holders 16. In addition, the weight 34 carried by the abrasion elements creates a known pressure or force between the abradant 14 and the fabric sample 15 mounted on the fabric sample holder 16, thereby, accelerating the abrading process.

In one advantageous embodiment, the upper surface of the fabric sample holder and, in some embodiments, the entire fabric sample holder may be formed of an at least partially optically transmissive material. Thus, the abrasion tester 10 of this embodiment also preferably includes means, such as a light source, for illuminating the optically transmissive portion of the fabric sample holder. As such, the fabric sample supported by the illuminated fabric sample holder is backlit during the abrasion process to allow the operator to more readily detect abrasion or wear of the fabric sample.

Figure 10:
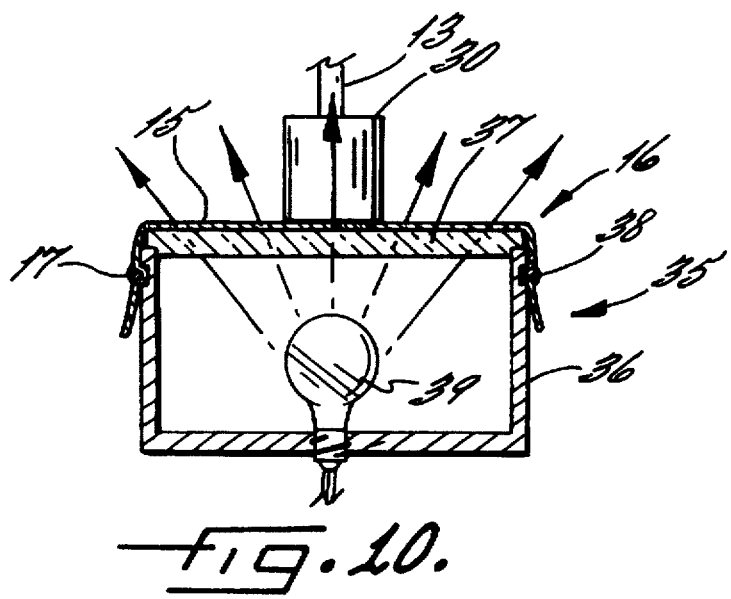
FIG. 10 is a cross sectional view of a fabric sample holder of one embodiment with directional arrows illustrating the backlighting of the fabric sample with a light bulb.
Figure 11:
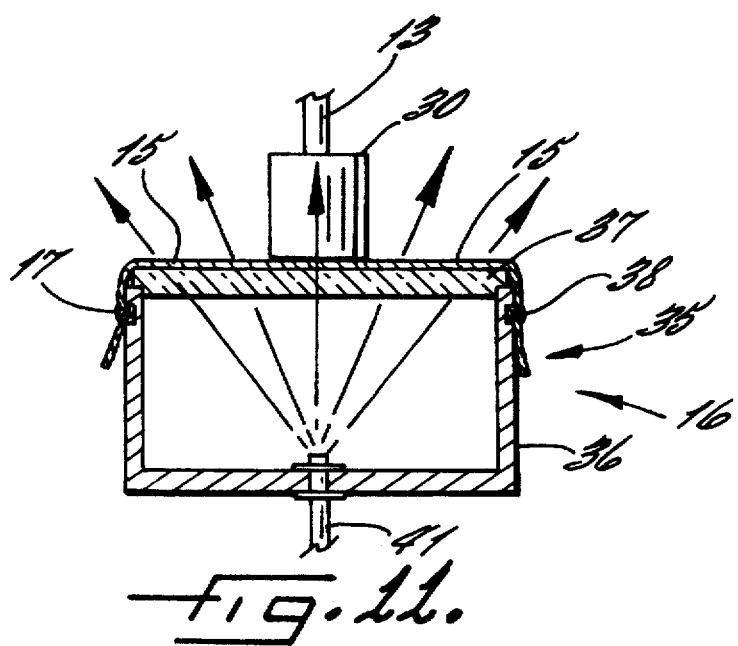
FIG. 11 is a cross sectional view of a fabric sample holder of another embodiment with directional arrows illustrating the backlighting of the fabric sample with an optical fiber.

As shown in FIGS. 10 and 11, for example, the fabric sample holder 16 of one embodiment includes a pedestal 35 having a cup-like base 36 and a top surface 37 covering the upwardly opening covering defined by the base. As described above, the exterior sidewalls of the base 36 can define a groove 38 for receiving an elastomeric ring 17 so as to securely mount a fabric sample 15 to the base. In a preferred embodiment, the top surface 37 is a disc that is formed of a material selected from a group consisting of a translucent material and a transparent material such that the disc is at least partially optically transmissive. Specifically, in one preferred embodiment, the top surface 37 may be formed from either polycarbonate resins such as a LEXAN® material or polymethyl methacrylate such as a PLEXI-GLASS® material. Alternately, the entire pedestal 35 may be formed of a material that is partially optically transmissive.

The fabric sample holder of this advantageous embodiment can also include a variety of different light sources. As is shown in FIG. 10, for example, the light source can include a light bulb 39 centrally positioned within the cavity defined by the pedestal 35 to illuminate the at least partially optically transmissive top surface 37, thereby backlighting the fabric sample 15. As will be apparent, the light bulb is connected to an external source of power by means of electrical wiring or cabling. Alternately, as is shown in FIG. 11, the light source can be remote from the fabric sample holder, but can illuminate the fabric sample holder by means of an optical fiber 41 that extends from the remote light source to a location inside the cavity defined by the pedestal 35. In either case, the backlighting illuminates the abrasion of the fabric sample 15, thus, increasing the accuracy with which the operator can view the fabric abrasion test results.

Thus, the fabric abrasion tester and associated abrading methods of the present invention permit fabric samples to be efficiently tested by minimizing disruptions in the testing process and correspondingly reducing the time and labor demanded during the testing process. More specifically, as a result of the optically transmissive motion plate and/or the backlighting of the fabric sample, the fabric abrasion tester and associated abrading methods of the present invention permit the abrading process to be monitored without halting the abrasion test and without lifting the motion plate as required by conventional Martindale-type abrasion testers.

In the drawings and the specification, there has been set forth a preferred embodiment of the invention wherein the abrasion elements are mounted in the optically transmissive motion plate and have abrasive lower surfaces for abrading the corresponding fabric samples. Although this embodiment is preferred, the present invention is not limited thereto and includes other embodiments within the spirit and scope of the present invention. Specifically, although less preferred, the fabric sample holders may be mounted in the optically transmissive motion plate with the fabric samples attached on lower surfaces of the fabric sample holders and contacting the corresponding adjacent abrasive surfaces. In this particular embodiment, the fabric abrasion holders may be raised to facilitate replacement of both the fabric samples and the abrasive surfaces in the same manner as the abrasive elements are raised according to the preferred embodiment described herein. Although specific terms are employed in the drawings and specification, these terms are used in a generic and descriptive sense only and not for purpose of limitation, the scope of the invention being set forth in the following claims.

That which is claimed is:

1. A fabric abrasion testing device for abrading a fabric sample in a predetermined manner comprising:
   at least one fabric sample holder for supporting the fabric sample;
   at least one abrasion element having an abrasive lower surface, said abrasion element having a predetermined weight for urging the abrasive lower element toward the fabric sample supported by a corresponding fabric sample holder;
   an optically transmissive motion plate comprised of a material selected from a group consisting of a translucent material and a transparent material such that abrasion of the fabric sample can be observed through said optically transmissive motion plate, said optically transmissive motion plate defining at least one aperture for mounting said abrasion element therethrough; and
   a motor, operably connected to said optically transmissive motion plate for moving said optically transmissive motion plate in a predetermined pattern relative to said at least one fabric sample holder such that said at least one abrasion element also moves in a predetermined pattern relative to the fabric sample mounted on the corresponding fabric sample holder.

2. A fabric abrasion testing device as defined in claim 1 wherein said fabric sample holder further comprises means for backlighting the fabric sample.

3. A fabric abrasion testing device as defined in claim 2 wherein said fabric sample holder further comprises a pedestal having an upper surface for supporting the fabric sample, wherein at least an upper portion of said pedestal is comprised of a material selected from a group consisting of a translucent material and a transparent material which is at least partially optically transmissive, wherein said fabric sample holder further comprises means for illuminating at least the upper portion of said pedestal such that the fabric sample supported by said fabric sample holder is backlit.

4. A fabric abrasion testing device as defined in claim 3 wherein said pedestal is comprised of a material selected from a group consisting of a translucent material and a transparent material which is at least partially optically transmissive.

5. A fabric abrasion testing device as defined in claim 3 wherein said upper surface of said pedestal is an at least partially optically transmissive disc.

6. A fabric abrasion testing device as defined in claim 2 wherein said means for backlighting the fabric sample comprises an optical fiber for delivering light to said fabric sample holder.

7. A fabric abrasion testing device as defined in claim 2 wherein said means for backlighting the fabric sample is a light bulb for delivering light to said fabric sample holder.

8. A fabric abrasion testing device for abrading a fabric sample in a predetermined manner comprising:
   at least one fabric sample holder for supporting the fabric sample;
   at least one abrasion element corresponding to said fabric sample holder having an abrasive surface;
   an optically transmissive motion plate comprised of a material selected from a group consisting of a translucent material and a transparent material such that abrasion of the fabric sample can be observed through said optically transmissive motion plate, said optically transmissive motion plate defining at least one aperture for mounting an element therethrough selected from the group consisting of said at least one abrasion element and said at least one fabric sample holder; and a motor, operably connected to said optically transmissive motion plate for moving said optically transmissive motion plate in a predetermined pattern such that said mounted element moves in a predetermined pattern relative to the corresponding element and said abrasive surface abrades said corresponding fabric surface.

9. A fabric abrasion testing device as defined in claim 8 further comprising at least one predetermined weight matched with a corresponding abrasion element and a corresponding fabric sample holder for urging the abrasive surface and fabric sample together.

10. A fabric abrasion testing device as defined in claim 8 wherein said at least one fabric sample holder further comprises means for backlighting the fabric sample.

11. A fabric abrasion testing device as defined in claim 10 wherein said at least one fabric sample holder further comprises a pedestal having an upper surface for supporting the fabric sample, and wherein at least an upper portion of said pedestal is comprised of a material selected from a group consisting of a translucent material and a transparent material which is at least partially optically transmissive.

12. A fabric abrasion testing device as defined in claim 11 wherein said entire pedestal is comprised of a material selected from a group consisting of a translucent material and a transparent material which is at least partially optically transmissive.

13. A fabric abrasion testing device as defined in claim 11 wherein said upper surface of said pedestal is an at least partially optically transmissive disk.

14. A fabric abrasion testing device as defined in claim 10 wherein said means for backlighting the fabric sample comprises an optical fiber for delivering light to said at least one fabric sample holder.

15. A fabric abrasion testing device as defined in claim 10 wherein said means for backlighting the fabric sample is a light bulb for delivering light to said at least one fabric sample holder.

* * * * *